United States Patent
Hansen et al.

(10) Patent No.: US 10,049,368 B2
(45) Date of Patent: Aug. 14, 2018

(54) SYSTEMS, METHODS AND COMPUTER PROGRAM PRODUCTS FOR PROVIDING COMPLIANT MESSAGING SERVICES

(75) Inventors: Michael Hansen, Apex, NC (US); Simon Dennison, Hertfordshire (GB); Sue Meyer, Apex, NC (US); Bipin Patel, Hertfordshire (GB); Timothy James Davis, Hertfordshire (GB)

(73) Assignee: ERESEARCHTECHNOLOGY, INC., Philadelphia, PA (US)

( * ) Notice: Subject to any disclaimer, the term of this patent is extended or adjusted under 35 U.S.C. 154(b) by 0 days.

(21) Appl. No.: 12/434,244

(22) Filed: May 1, 2009

(65) Prior Publication Data
US 2009/0281829 A1 Nov. 12, 2009

Related U.S. Application Data

(60) Provisional application No. 61/051,447, filed on May 8, 2008.

(51) Int. Cl.
| | |
|---|---|
| *G06Q 50/00* | (2012.01) |
| *G06Q 30/02* | (2012.01) |
| *G06Q 10/10* | (2012.01) |
| *G06Q 50/22* | (2018.01) |
| *H04L 12/58* | (2006.01) |

(52) U.S. Cl.
CPC .......... *G06Q 30/02* (2013.01); *G06Q 10/107* (2013.01); *G06Q 50/22* (2013.01); *H04L 51/00* (2013.01)

(58) Field of Classification Search
CPC ...... H04L 29/06; H04L 12/5885; H04L 51/18
USPC .......................................... 705/2–3; 703/2–3
See application file for complete search history.

(56) References Cited

U.S. PATENT DOCUMENTS

| | | |
|---|---|---|
| 5,778,882 A | 7/1998 | Raymond et al. |
| 6,095,985 A | 8/2000 | Raymond et al. |
| 6,138,008 A * | 10/2000 | Dunn et al. ................ 455/417 |
| 6,282,441 B1 | 8/2001 | Raymond et al. |
| 6,440,069 B1 | 8/2002 | Raymond et al. |
| 6,640,134 B2 | 10/2003 | Raymond et al. |
| 6,879,970 B2 | 4/2005 | Shiffman et al. |
| 7,273,454 B2 | 9/2007 | Raymond et al. |
| 7,415,447 B2 | 8/2008 | Shiffman et al. |
| 7,725,816 B2 * | 5/2010 | Cottrille et al. ............. 715/234 |

(Continued)

FOREIGN PATENT DOCUMENTS

| | | | |
|---|---|---|---|
| WO | WO-9625877 A2 | 8/1996 | |
| WO | WO 01/78345 A1 * | 10/2001 | ............. H04L 29/00 |
| WO | WO 2007/056822 A1 * | 5/2007 | ............. G06Q 10/00 |

OTHER PUBLICATIONS

Office Action dated Jan. 22, 2015 for U.S. Appl. No. 13/838,698.

(Continued)

*Primary Examiner* — Joy Chng
(74) *Attorney, Agent, or Firm* — Wilson, Sonsini, Goodrich & Rosati (57) ABSTRACT

Systems, methods and computer program products for providing compliant messaging services are disclosed. Methods according to some embodiments include receiving input data from a campaign sponsor, encrypting at least a portion of the input data, generating a message schedule that includes message content, recipient identification data and temporal data corresponding to a plurality of messages, and sending and/or receiving one of the plurality of messages to and/or from a corresponding recipient.

29 Claims, 4 Drawing Sheets

(56) References Cited

U.S. PATENT DOCUMENTS

| | | | |
|---|---|---|---|
| 7,873,589 B2 | 1/2011 | Shiffman et al. | |
| 8,065,180 B2 | 11/2011 | Hufford et al. | |
| 8,145,519 B2 | 3/2012 | Hufford et al. | |
| 8,273,019 B2 | 9/2012 | Crowley et al. | |
| 8,380,531 B2 | 2/2013 | Paty et al. | |
| 8,433,605 B2 | 4/2013 | Hufford et al. | |
| 8,533,029 B2 | 9/2013 | Hufford et al. | |
| 9,075,900 B2 | 7/2015 | Wilson et al. | |
| 9,129,215 B2 | 9/2015 | Shiffman et al. | |
| 9,483,618 B2 | 11/2016 | Brincat et al. | |
| 2002/0087704 A1* | 7/2002 | Chesnais et al. | 709/228 |
| 2002/0156640 A1 | 10/2002 | Hufford et al. | |
| 2003/0036683 A1* | 2/2003 | Kehr et al. | 600/300 |
| 2004/0186750 A1* | 9/2004 | Surbey et al. | 705/4 |
| 2005/0004814 A1* | 1/2005 | Seltzer | 705/2 |
| 2006/0174111 A1* | 8/2006 | Burns | 713/166 |
| 2007/0149214 A1 | 6/2007 | Walsh et al. | |
| 2008/0013701 A1 | 1/2008 | Yoffie et al. | |
| 2008/0013705 A1* | 1/2008 | Yoffie et al. | 379/201.12 |
| 2013/0157244 A1 | 6/2013 | Eger et al. | |
| 2013/0159010 A1 | 6/2013 | Paty et al. | |
| 2013/0268287 A1 | 10/2013 | Hufford et al. | |
| 2014/0108032 A1 | 4/2014 | Hufford et al. | |
| 2015/0178473 A1 | 6/2015 | Hufford et al. | |
| 2015/0178474 A1 | 6/2015 | Hufford et al. | |
| 2016/0034541 A1 | 2/2016 | Shiffman et al. | |
| 2016/0284058 A1 | 9/2016 | Calderwood et al. | |

OTHER PUBLICATIONS

Office Action dated Feb. 8, 2016 for U.S. Appl. No. 13/838,698.
Office Action dated Jun. 24, 2015 for U.S. Appl. No. 13/838,698.
Office Action dated Jun. 28, 2017 for U.S. Appl. No. 13/801,853.
Co-pending U.S. Appl. No. 11/002,046, filed Jan. 12, 2014.
Co-pending U.S. Appl. No. 15/291,103, filed Oct. 12, 2016.
Co-pending U.S. Appl. No. 15/468,613, filed Mar. 24, 2017.
EResearchTechnology GmbH. MasterScope ©: Diagnostic Platform for Centralized Spirometry, ECG and Home Monitoring. © 2014 eResearchTechnology GmbH. Rev. 02, May 30, 2014. 4 pages.
EResearchTechnology GmbH. SpiroPro © CT: Handheld Spirometer and Pulse Oximeter. © 2014 eResearchTechnology GmbH. Rev. 01, Jul. 2014. 2 pages.
ERT ©. ERT Introduces Updated Diagnostic Platform for Centralized Spirometry, ECG, and Home Monitoring in Respiratory Clinical Trials. Web article. Jun. 16, 2014. 4 pages. URL:<https://www.ert.com/ert-introduces-updated-diagnostic-platform-for-centralized-spirometry-ecg-and-home-monitoring-in-respiratory-clinical-trials/>.
Office action dated Jan. 3, 1996 for U.S. Appl. No. 08/394,157.
Office action dated Jan. 4, 2012 for U.S. Appl. No. 12/177,540.
Office action dated Jan. 8, 2008 for U.S. Appl. No. 11/002,046.
Office action dated Jan. 25, 2016 for U.S. Appl. No. 14/792,126.
Office action dated Jan. 26, 2007 for U.S. Appl. No. 09/840,730.
Office action dated Jan. 29, 2009 for U.S. Appl. No. 09/840,730.
Office action dated Feb. 7, 2006 for U.S. Appl. No. 10/693,232.
Office Action dated Feb. 8, 2017 for U.S. Appl. No. 14/670,261.
Office action dated Feb. 9, 2006 for U.S. Appl. No. 09/825,533.
Office action dated Feb. 10, 1997 for U.S. Appl. No. 08/394,157.
Office action dated Feb. 19, 2010 for U.S. Appl. No. 11/844,632.
Office action dated Feb. 20, 2015 for U.S. Appl. No. 13/688,962.
Office action dated Mar. 9, 2012 for U.S. Appl. No. 12/509,318.
Office action dated Mar. 12, 2013 for U.S. Appl. No. 13/603,035.
Office action dated Mar. 13, 2012 for U.S. Appl. No. 12/965,719.
Office action dated Mar. 20, 2015 for U.S. Appl. No. 13/670,151.
Office action dated Apr. 3, 2009 for U.S. Appl. No. 09/825,533.
Office Action dated Apr. 4, 2017 for U.S. Appl. No. 14/792,126.
Office action dated Apr. 11, 2007 for U.S. Appl. No. 10/693,232.
Office action dated Apr. 19, 2006 for U.S. Appl. No. 11/002,046.
Office action dated Apr. 21, 2016 for U.S. Appl. No. 13/670,151.
Office action dated Apr. 29, 2010 for U.S. Appl. No. 09/825,533.
Office action dated May 2, 2000 for U.S. Appl. No. 09/447,986.
Office Action dated May 5, 2017 for U.S. Appl. No. 14/579,670.
Office action dated May 8, 2014 for U.S. Appl. No. 12/965,719.
Office action dated May 18, 1999 for U.S. Appl. No. 09/001,032.
Office action dated May 20, 2008 for U.S. Appl. No. 09/825,533.
Office action dated May 20, 2016 for U.S. Appl. No. 13/801,853.
Office Action dated May 22, 2017 for U.S. Appl. No. 13/670,151.
Office action dated May 26, 2015 for U.S. Appl. No. 13/801,853.
Office action dated Jun. 7, 2011 for U.S. Appl. No. 12/177,540.
Office action dated Jun. 8, 2000 for U.S. Appl. No. 09/447,986.
Office Action dated Jun. 8, 2017 for U.S. Appl. No. 13/688,962.
Office action dated Jun. 16, 2008 for U.S. Appl. No. 09/840,730.
Office action dated Jun. 18, 2007 for U.S. Appl. No. 11/002,046.
Office action dated Jun. 26, 2014 for U.S. Appl. No. 13/801,853.
Office action dated Jul. 2, 2014 for U.S. Appl. No. 13/670,151.
Office action dated Jul. 10, 1997 for U.S. Appl. No. 08/394,157.
Office action dated Jul. 12, 2005 for U.S. Appl. No. 11/002,046.
Office action dated Jul. 15, 2002 for U.S. Appl. No. 09/940,129.
Office action dated Jul. 17, 2007 for U.S. Appl. No. 09/840,730.
Office action dated Jul. 19, 2006 for U.S. Appl. No. 10/693,232.
Office action dated Aug. 31, 2016 for U.S. Appl. No. 13/670,151.
Office action dated Sep. 3, 2015 for U.S. Appl. No. 13/688,962.
Office action dated Sep. 8, 2006 for U.S. Appl. No. 09/825,533.
Office action dated Sep. 18, 2013 for U.S. Appl. No. 13/801,853.
Office Action dated Sep. 28, 2016 for U.S. Appl. No. 14/792,126.
Office action dated Sep. 29, 1998 for U.S. Appl. No. 09/001,032.
Office action dated Oct. 4, 2005 for U.S. Appl. No. 09/840,730.
Office action dated Oct. 4, 2011 for U.S. Appl. No. 12/965,719.
Office action dated Oct. 9, 2015 for U.S. Appl. No. 13/801,853.
Office action dated Oct. 11, 2012 for U.S. Appl. No. 12/965,719.
Office Action dated Oct. 13, 2016 for U.S. Appl. No. 14/579,670.
Office action dated Oct. 22, 2014 for U.S. Appl. No. 13/801,853.
Office action dated Nov. 14, 2007 for U.S. Appl. No. 11/324,504.
Office Action dated Nov. 16, 2016 for U.S. Appl. No. 13/688,962.
Office action dated Nov. 17, 2014 for U.S. Appl. No. 13/953,503.
Office action dated Nov. 22, 2013 for U.S. Appl. No. 13/801,853.
Office action dated Nov. 25, 2011 for U.S. Appl. No. 12/509,318.
Office action dated Nov. 26, 2010 for U.S. Appl. No. 09/825,533.
Office action dated Dec. 5, 2006 for U.S. Appl. No. 11/002,046.
Office action dated Dec. 19, 2002 for U.S. Appl. No. 09/940,129.
Office action dated Dec. 20, 2007 for U.S. Appl. No. 09/840,730.
Office action dated Dec. 30, 2010 for U.S. Appl. No. 12/177,540.
Office Action dated Jan. 17, 2018 for U.S. Appl. No. 13/688,962.
Office Action dated Sep. 5, 2017 for U.S. Appl. No. 14/579,574.
Office Action dated Sep. 8, 2017 for U.S. Appl. No. 14/670,261.
Office Action dated Nov. 29, 2017 for U.S. Appl. No. 14/579,670.

* cited by examiner

SYSTEMS, METHODS AND COMPUTER PROGRAM PRODUCTS FOR PROVIDING COMPLIANT MESSAGING SERVICES

CROSS-REFERENCE TO RELATED APPLICATIONS

The present non-provisional patent application claims the benefit of and priority from U.S. Provisional Application No. 61/051,447, filed on May 8, 2008, the entire contents of which are hereby incorporated herein by reference.

FIELD OF THE INVENTION

The present invention relates generally to communication and, more particularly, to systems, methods and computer program products for providing messaging services.

BACKGROUND

Many industries may utilize and/or rely on communications with multiple classes of users. For example, the healthcare and pharmaceutical industries may rely on communications between various classes including healthcare providers, such as doctors and/or nurses, patients, prospective patients, and/or clients, such as, for example, healthcare research organizations, medical device manufacturers and/or pharmaceutical companies, among others. Advances in technology have provided for wireless communication systems using, for example, mobile terminals. However, such systems may not provide safeguards that may be required under strictly regulated industries, such as, for example, the healthcare and/or pharmaceutical industries. Accordingly, currently available systems and methods may not be suitable for use in applications that require compliance with industry-specific rules and regulations.

SUMMARY

Pursuant to some embodiments of the present invention, systems, methods and computer program products for providing compliant messaging services are disclosed. Some embodiments include methods of providing healthcare compliant messaging services that include receiving input data corresponding to a campaign from a campaign sponsor, encrypting at least a portion of the input data, and generating, under the control of one or more computer systems, a message schedule that is based on the input data and that includes message content, recipient identification data and temporal data corresponding to multiple messages. Methods may include sending one of the messages to a corresponding recipient, confirming a delivery of at least one of the messages sent to the recipient and receiving a response from the corresponding recipient to the one of the messages. Methods may include validating at least one of the messages and/or the response from the corresponding recipient. Some embodiments provide that validating includes comparing the messages and/or the response to multiple valid messages. Some embodiments include generating an audit trail that is configured to create a historical record corresponding to each of the messages and generating a unique identifier corresponding to the one of the messages.

Some embodiments of the present invention include methods for providing compliant messaging services. Such methods may include receiving input data corresponding to a campaign from a campaign sponsor, encrypting at least a portion of the input data, generating, under the control of one or more computer systems, a message schedule that is based on the input data and that includes message content, recipient identification data and temporal data corresponding to multiple messages. Some embodiments include sending one of the messages to a corresponding recipient.

Some embodiments include confirming a delivery of at least one of the messages sent to the recipient. Some embodiments include validating at least one of the messages and/or a response from the corresponding recipient, wherein validating includes comparing the message and/or response to multiple valid messages.

Some embodiments include, upon receiving indication of delivery failure of the at least one of the messages, sending the at least one of the messages via a different redundant communication network route and/or channel. In some embodiments, receiving indication of delivery failure of the at least one of the messages includes failure to confirm a delivery of the at least one of the messages. Some embodiments provide that receiving indication of delivery failure of the at least one of the messages includes receiving indication of delivery failure from a communications network resource.

Some embodiments include generating an audit trail that is configured to create a historical record corresponding to each of the messages. In some embodiments, the audit trail includes message version data, message timestamp data corresponding to any changes to the message, delivery attempt data including corresponding timestamp data, response data corresponding to messages received by compliant message module and/or user identification data.

Some embodiments provide that the compliant messaging services are compliant with healthcare and/or pharmaceutical service specific requirements.

Some embodiments include receiving a response from the corresponding recipient to the one of the plurality of messages. Some embodiments include generating unique identifiers corresponding to ones of the messages.

Some embodiments of the present invention include a healthcare compliant message system for providing healthcare compliant messaging services. Embodiments of such a system include a campaign message manager that receives campaign data corresponding to a campaign by a campaign sponsor and subject data corresponding to study subjects who are participating in the campaign, and generates message schedule data corresponding to the campaign data and the subject data and that defines message delivery and message content information. A system may include a compliant message module that receives the message schedule data, transmits messages that correspond to the message schedule to respective mobile terminals, and receives a message originating from at least one of the mobile terminals responsive to the transmitted message.

In some embodiments, the compliant message module is further configured to transmit a message to the mobile terminal that is responsive to a mobile terminal originated message that is an initiating message responsive to an external information source.

Some embodiments provide that the campaign message manager includes a user interface that receives the campaign data via an administrative user, wherein the user interface includes an end user portion that receives the study data, and an enrollment module that uses subject data that is received via the user interface to populate an enrolled study subject database corresponding to enrolled study subjects. In some embodiments, the campaign message manager includes a message schedule generator that uses the campaign data via the user interface and the enrolled study subject database to generate message schedule data.

In some embodiments, the message schedule data includes at least one message schedule, message content, at least one reminder message, at least one message language identifier, message format and/or location-based temporal information.

Some embodiments provide that the campaign message manager includes a communication module that communicates message schedule data to the compliant message module.

In some embodiments, the compliant message module includes a message transmitter that transmits messages to at least one mobile terminal according to the message schedule, a message receiver that receives messages originated by at least one mobile terminal, and an audit trail module that generates and maintains an audit trail corresponding to messages that are transmitted to the at least one mobile terminal and received by the compliant message module. Some embodiments provide that the audit trail includes message version data, message timestamp data corresponding to any changes to the message, delivery attempt data including corresponding timestamp data, response data corresponding to messages received by compliant message module and/or user identification data.

Some embodiments include a validation module that is operable to validate received messages originated by the at least one mobile terminal to determine if ones of the received messages are valid responses to respective ones of the transmitted messages, wherein the audit trail further includes validation data.

In some embodiments, the message schedule data includes a message frequency restriction corresponding to transmitted messages. Some embodiments provide that the message frequency restriction restricts the quantity of messages that can be transmitted within a defined temporal duration.

In some embodiments, the campaign message manager generates the message schedule data via at least one message template that includes a predefined message format and wherein the campaign data includes at least one message template identifier that corresponds to the at least one message template. Some embodiments provide that the at least one message template includes a multilingual function such that at least one message template is operable to be expressed and/or receive data in multiple languages. In some embodiments, the at least one message template includes multiple customizable placeholders.

Some embodiments include computer program products for providing compliant messaging services, the computer program product comprising a computer usable storage medium having computer readable program code embodied in the medium, the computer readable program code configured to carry out the methods described herein.

DETAILED DESCRIPTION

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. As used herein, the term "and/or" includes any and all combinations of one or more of the associated listed items.

Pursuant to embodiments of the present invention, systems and methods are provided for providing compliant messaging services. Compliance may be required for applications used in, for example, healthcare and/or pharmaceutical industries. In some embodiments, a sponsor, such as a pharmaceutical provider, for example, may initiate and/or manage a campaign such as, for example, a clinical and/or marketing study regarding a new drug and/or drug application and/or disease condition. In some embodiments, a campaign may include a prescription reminder service. In this regard, a campaign may include a series of events and/or operations undertaken to achieve a specific goal. As described herein, campaigns may be directed to gathering and/or disseminating information and/or data corresponding to a clinical and/or marketing study regarding a new drug and/or drug application, disease condition and/or a prescription reminder service, among others. Concomitant with such studies may be strict requirements including audit trails, validation, authentication and/or confidentiality, among others. Additionally, as a practical matter, global connectivity, sufficient encryption and performance, multi-lingual capability and/or integration flexibility may be necessary as well. In this regard, a trusted third party to manage the management, data, communications, and/or compliance issues associated with such campaigns may be beneficial. For example, in some regulatory environments, sponsors may be prohibited from having direct contact with and/or storing any customer, subject and/or patient data, among others.

In some embodiments of the present invention, the compliant messaging services disclosed herein may be utilized for patient recruitment for clinical studies. For example, prospective subjects may be pre-screened via responses to text messages including specific pre-screening questions. Such questions may include queries regarding age, gender, weight, height, non-smoker/smoker and/or ethnicity, among others. In this manner, only prospective study subjects meeting the initial study criteria may be directed to contact a call center for additional evaluation. Prospective candidates may be determined by health provider lists, and/or responses to advertisements among others. In some embodiments, a geographic location of a subject may be determined using, for example, a location identifier, such as a post code and/or a zip code among others. Some embodiments provide that the geographic location may be used to direct a request to a locally proximate hospital, call center, and/or clinic, among others.

Figure 1:
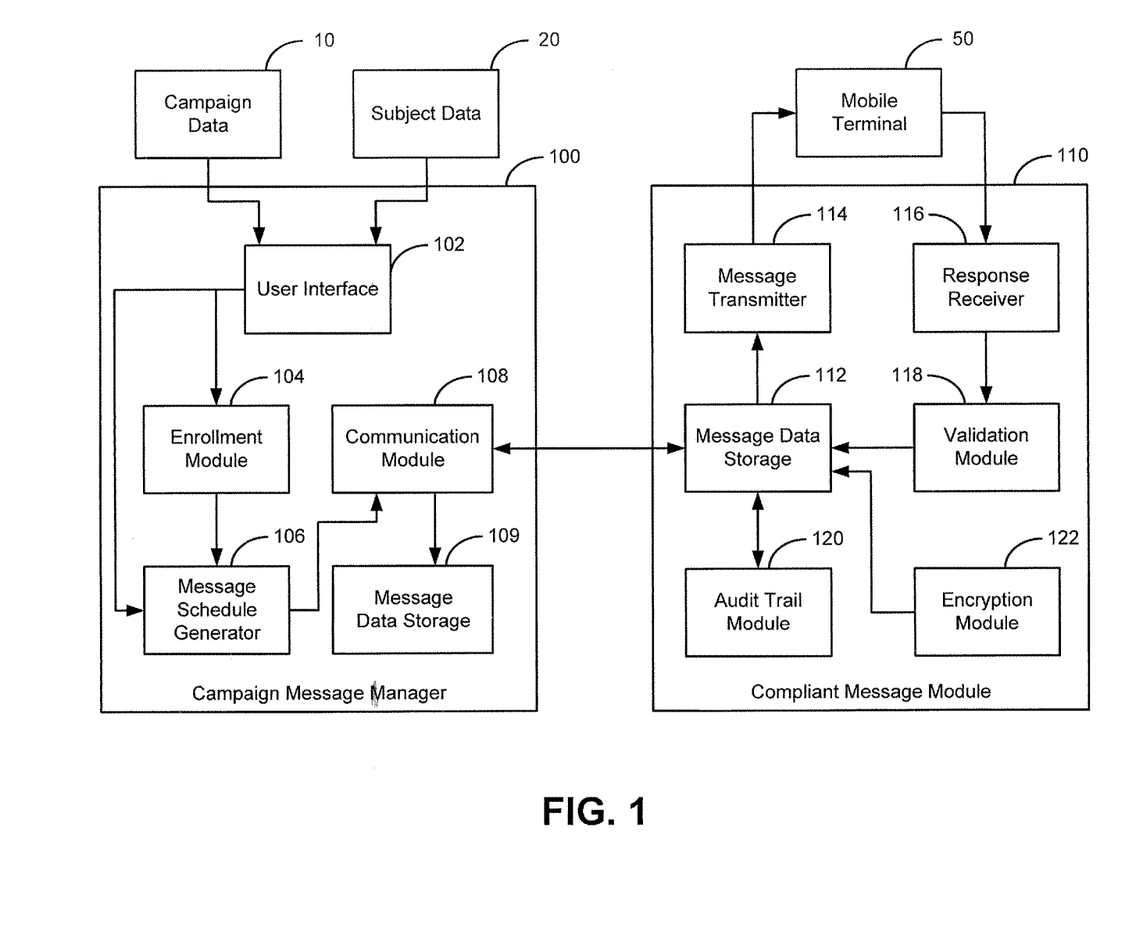
FIG. 1 is a block diagram illustrating a system for providing compliant messaging services according to some embodiments of the present invention.

Reference is now made to FIG. 1, which is a block diagram illustrating a system for providing compliant messaging services according to some embodiments of the present invention. A campaign message manager 100 may be configured to include a user interface 102. The user interface 102 may be configured to receive campaign data 10 from, for example, a study administrator who may be administering and/or managing a study or campaign, a site administrator and/or a system administrator, among others. In some embodiments, a system administrator may input campaign data 10 through an administrative interface portion that may be used for the creation and setup of the study (campaign), the site, and/or the user.

In some embodiments, the user may include a doctor, nurse, patient and/or other client representative, among others. The user interface 102 may also include an end user portion that may be used by the client representative to perform functions related to study subjects and/or schedules. In some embodiments, subjects may include patients in a healthcare related campaign and/or study. In this regard, subject data 20 may be received via the end user portion of the user interface 102.

In some embodiments, the campaign message manager 100 may include an enrollment module 104 that may use the subject data 20 received through the user interface 102 to populate a data base (not shown). The enrollment module 104 may be used to capture and/or store subject data including, for example, name, contact information, and/or study specific information, among others. In some embodiments, the enrollment module 104 may provide a unique subject identifier that may be used to identify the subject without compromising any of the subject's confidential information.

Some embodiments provide that a message schedule generator 106 may be included to generate message schedules, message content, reminders, message language(s), message format, and/or communication protocol, among others. The message schedule generator 106 may use the campaign data 10 and the subject data 20 to generate complete message schedule data. Some embodiments provide that the message schedule generator 106 generates message schedules according to one or more local time zones of respective recipients. A communication module 108 may be configured to communicate the message schedule data to a compliant message module 110 that is configured to deliver and/or manage the delivery of the messages in compliance with regulatory requirements. In some embodiments, the message schedule data may include message content, delivery temporal data, a subject identifier, message format and/or location-based temporal information (e.g., time zones), among others. Some embodiments provide that message data storage 109 is configured to store data corresponding to messages that are scheduled by the message schedule generator 106 and/or communicated via the communication module 108. In some embodiments, the message data storage 109 may be a portion of a data storage structure and/or device that is configured to store subject data 20 and/or campaign data 10.

The compliant message module 110 may include message data storage 112 that is configured to receive and/or store the message data from the campaign message manager 100. In some embodiments, the message data storage 112 may operate in conjunction with an audit trail module 120 that may be configured to generate and maintain an audit trail for all messages. In some embodiments, the audit trail may include all versions of a message including timestamp data corresponding to any changes, delivery attempt data including timestamps of all message delivery attempts, response data corresponding to any responses, validation data, user name, and/or database changes, among others.

The message data storage 112 may be configured to operate in conjunction with an encryption module 122 that may be configured to provide encryption of message data and/or subject data 20 for transmission and/or storage. For example, in some embodiments, phone numbers and messages may be encrypted at the data storage level in a data structure such as, for example, a database.

The compliant message module 110 may include a message transmitter 114 that is configured to transmit messages at times and dates corresponding to the message schedule. The message transmitter 114 may be configured to operate using data communication standards including Extensible Markup Language (XML) and/or Hypertext Transfer Protocol over Secure Socket Layer (HTTPS), among others. The message transmitter 114 may be configured to provide global interconnectivity using multiple communications networks worldwide. In some embodiments, the message transmitter 114 may include an architecture that processes more than 500 messages per second in more than 200 countries via access to more than 600 system operators. In some embodiments, the message transmitter 114 may use open communications, network and/or device standards to reduce risks associated with integration complexity. In this manner, messages may be delivered to mobile terminals 50 in compliance with regulatory requirements.

In some embodiments, the message transmitter 114 may be configured to provide redundant communications network paths to transmit messages to the mobile terminal 50. For example, some embodiments provide that if the compliant message module 110 determines that the message was not received by the mobile terminal 50, then the message transmitter 114 may resend the message to the mobile terminal 50 via another communications network path and/or route. In this manner, the messaging services may be less susceptible to interruptions from communications network related outages and/or performance issues. Some embodiments provide that the compliant message module 110 may determine that the message was not received by the mobile terminal 50 based on a lack of confirmation receipt. In some embodiments, the compliant message module 110 may determine that the message was not received by the mobile terminal 50 based on information received from a communications network resource.

In some embodiments, a mobile terminal 50 may include a subject mobile terminal corresponding to a subject participating in a study. In some embodiments, a mobile terminal 50 may include a mobile terminal corresponding to a provider, administrator and/or sponsor. Some embodiments provide that the mobile terminal 50 may include a personal digital assistant (PDA), cell phone, pager and/or a machine that does not include a direct human communication interface. For example, the mobile terminal 50 may include a machine such as a software and/or hardware device that is operable to monitor glucose, blood pressure and/or other physiological conditions that does not include a direct human communication interface as may typically be found in a cell phone. In this regard, the mobile terminal 50 may be operable to trigger an event on the machine and/or send/receive a message containing data from and/or corresponding to the mobile terminal 50. In some embodiments, the mobile terminal 50 may provide 2-way communication without a direct human communication interface. For example, some embodiments provide that a physiological condition value range may be transmitted to the mobile terminal 50 and, if a measured corresponding physiological condition value is not within the range, an event may be triggered and a communication may be transmitted by the mobile terminal 50.

The compliant message module 110 may include a response receiver 116 that is configured to receive response messages that originate from mobile terminals 50. For example, in the case that a reminder message regarding an upcoming appointment is transmitted to the mobile terminal 50, a response might include a delivery confirmation indicating that the message was received and/or an indication as to whether the subject will be at the appointment. The compliant message module 110 may include a validation module 118 that is configured to validate a response that originates from a mobile terminal 50. For example, the content of a valid response may be specific to the sent message. In some embodiments, responding to a message may include initiating a logical response sequence that is responsive to the content of a received message. For example, in some embodiments, email may be sent to a provider if a subject is unable to keep a scheduled appointment. In some embodiments, a text message may be sent back to a subject requesting additional information and/or data. Some embodiments provide that the validation module 118 can accept or reject responses from the mobile terminal. In some embodiments, the validation module 118 may prompt the mobile terminal 50 for a valid response. For example, when an invalid response is received, the validation module 118 may prompt the mobile terminal 50 for a valid response.

The validation module 118 and/or the response receiver 116 may be configured to transmit response data and/or validation data to message data storage 112. The response data may be maintained in the audit trail by virtue of the audit trail module 120. In some embodiments, the encryption module 122 may provide encryption for all or portions of the response data before storage.

Response data may be communicated from the compliant message module 110 to the campaign message manager 100, which may be configured to store the response data in the message data storage 109. In some embodiments, the transmitted message may be referred to as a mobile terminating (MT) message and the response message may be referred to as a mobile originating (MO) message. In some embodiments, the campaign message manager 100 may request that the compliant message module 110 provide message delivery status regarding a MO and/or a MT message. Some embodiments provide that when confirmation of delivery of the MT message is received, the MT message may be deleted from message data storage 112. In some embodiments, regulatory requirements may dictate that captured clinical data in a mobile terminal be deleted after the clinical data is transferred to the compliant message module 110.

In some embodiments, regulatory requirements may dictate that captured clinical data may only reside in limited configurations. For example, regulations may require clinical data that is captured on a mobile terminal to be destroyed when the data is transferred to another data repository. In some embodiments, a message may include a self executing delete function that may be initiated by temporal, access, and/or transmission events. In this manner a message may include a self-destruct feature to remove traces of the message when, for example, it is transmitted to and/or receipt is confirmed by another data repository.

In some embodiments, any of a plurality of encryption schemes may be utilized to provide secure, encrypted messages. For example, some embodiments provide that a secure key may be provided to a mobile and/or other terminal for decrypting subsequent messages. In this manner, regulatory compliance directed to encryption requirements may be provided.

In some embodiments, a MO message may indicate that an appointment needs to be rescheduled. In such cases, additional MT messages may be generated responsive to this condition. In some embodiments, the subject may be directed to call a provider facility to reschedule the appointment. In some embodiments, the MT message may be a query as to how a subject is feeling. A valid MO message responsive to such a query may be limited to a finite set of responses, such as, for example, "Well", "Poorly", and/or "OK", among others. Additionally, to accurately associate a MO message to a specific MT message, the MT message may include a study-specific and/or message-specific time-out function and/or unique identifier. In some embodiments, the time-out function may recall the MT message if confirmation delivery is not received within a certain time from the transmission of the MT message. In some embodiments, the time-out function may trigger the compliant message module 110 to resend the MT message one of more times.

As discussed herein, the compliant message module 110 may operate in conjunction with a campaign message manager 100. In some embodiments, the campaign message manager 100 may be implemented as a stand alone application and/or in a dedicated server that is distinct from operations of study sponsors and/or clients. Some embodiments provide that the campaign message module 100 may be installed and/or hosted within a sponsor and/or client facility and/or equipment and be used and/or administered on-site by sponsor and/or client personnel. However, embodiments herein are not so limited. For example, reference is now made to FIG. 2, which is a block diagram of a system for providing compliant messaging services according to some embodiments of the present invention.

Figure 2:
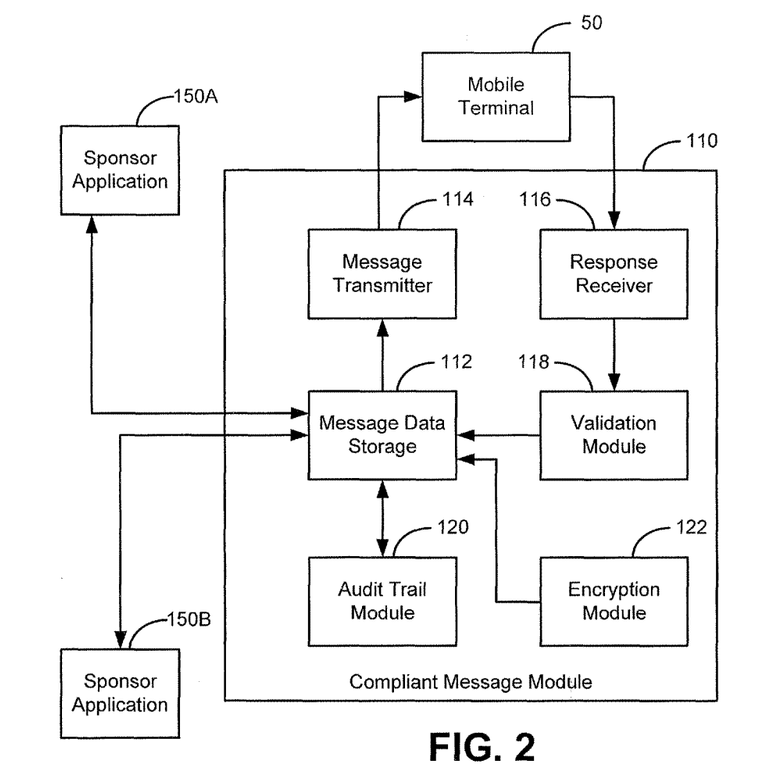
FIG. 2 is a block diagram of a system for providing compliant messaging services according to some embodiments of the present invention.

In some embodiments, the compliant message module 110 may operate in cooperation with sponsor applications 150A-B associated with multiple different respective sponsors. In some embodiments, sponsor may include pharmaceutical manufacturers, wholesalers, retailers and/or distributors and/or medical device manufacturers, wholesalers, retailers and/or distributors. For example, a first sponsor application 150A may correspond to a pharmaceutical company that is sponsoring a campaign for a clinical study corresponding to one of their proposed, existing and/or historical pharmacological offerings. A second sponsor application 150B may correspond to a research clinic conducting a subject recruitment campaign for a planned clinical trial. In this regard, the compliant messaging module 110 may provide the compliant messaging functions as discussed above regarding FIG. 1 associated with each of the two different sponsor applications 150A-B.

Figure 3:
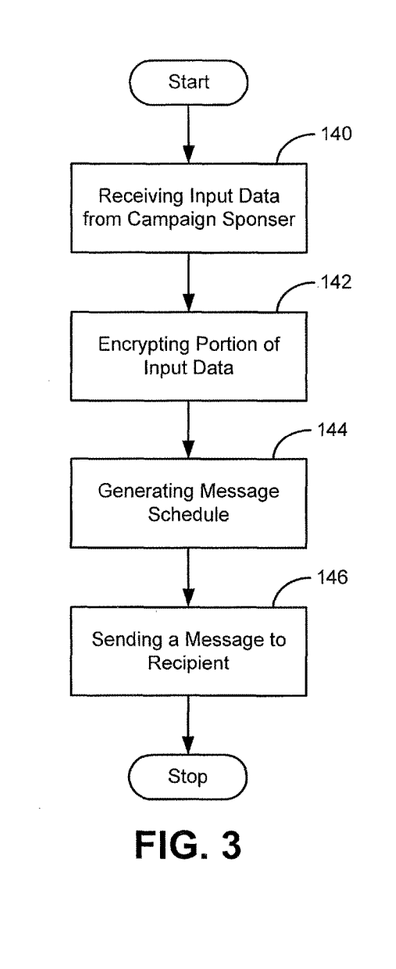
FIG. 3 is a block diagram illustrating operations for providing compliant messaging services according to some embodiments of the present invention.

Reference is now made to FIG. 3, which is a block diagram illustrating operations for providing compliant messaging services according to some embodiments of the present invention. Input data is received from a campaign sponsor (block 140). In some embodiments, the input data may include message data, subject data, campaign data, schedule data, login data, client data, unique identifier, metadata and/or user data, among others. Operations include encrypting at least a portion of the input data (block 142). In some embodiments, encrypting includes encrypting data prior to storage in a data storage structure, media and/or device. In some embodiments, encrypting includes encrypting a portion of the data that includes message content.

Some embodiments include generating a message schedule that includes message content, recipient identification data and temporal data corresponding to multiple messages (block 144). The message schedule may include content, delivery times and delivery conditions corresponding to reminder messages, status request messages, and/or confirmation messages, among others. For example, a subject may be sent a MT message including a reminder of an upcoming appointment and/or a reminder to take a specific medication. In some embodiments, the MT message may seek a responsive MO message indicating a subject's status, such as, for example, how the subject is feeling and/or whether the subject will be at a scheduled appointment, among others.

Some embodiments include sending one of the multiple messages to a corresponding recipient (block 146). In some embodiments, the corresponding recipient may be a subject and/or potential subject of a campaign, such as a clinical study and/or a study recruiting campaign. Some embodiments may include confirming a delivery of at least one of the multiple messages. In some embodiments, the delivery confirmation and/or message content may be sent to the campaign sponsor and/or maintained in a messaging service database. Some embodiments provide that delivery confirmation and/or message content may be provided and/or reported online via a network such as, for example, the Internet. In this manner, a sponsor may access delivery confirmation and/or content in a convenient and/or secure manner. In some embodiments, a logical sequence may be initiated responsive to the content of the MO message and/or delivery confirmation.

Some embodiments may include, upon receiving indication of delivery failure of the at least one of the multiple messages, sending the at least one of the multiple messages via a different redundant communication network route and/or channel. In some embodiments, receiving indication of delivery failure of the at least one of message may include a failure to confirm a delivery of the at least one message. Some embodiments provide that receiving indication of delivery failure of the message may include receiving indication of delivery failure from a communications network resource. In this manner, redundant delivery paths may be provided to enhance the reliability of the messaging operations.

Some embodiments provide that a MT message may be responsive to an unprompted MO message. For example, an unprompted MO message maybe initiated by a user responsive to, for example, an advertisement that may be received by the user via one or more advertising media such as magazines, newspaper, television, internet and/or radio, among others.

Some embodiments include generating an audit trail that is configured to create a historical record corresponding to each of the messages. In some embodiments, the audit trail may include a history that captures all modifications, generation and/or transmissions of each message and/or the timestamp corresponding to each of the activities, user name and/or events. In some embodiments, the audit trail may include data that is encrypted in compliance with regulatory requirements.

In some embodiments, the compliant messaging service may be configured to comply with healthcare service specific requirements. For example, healthcare services may be regulated by codes and/or statutes including the Health Insurance Portability and Accountability Act (HIPPA) and/or rules promulgated by the Department of Health and Human Services (HHS). For example, HHS rules may include a privacy rule, which may establish regulations for the use and disclosure of Protected Health Information (PHI), and a security rule, which may deal specifically with Electronic Protected Health Information (EPHI) and identify three types of security safeguards required for compliance, including, for example, administrative, physical, and/or technical safeguards. In some embodiments, healthcare services may be regulated by the Food and Drug Administration via, for example, 21 C.F.R. § 11. Although discussed in the context of healthcare specific services, however, the disclosure herein is not so limited.

Some embodiments include receiving a response from a subject via a mobile terminal. As discussed above regarding FIG. 1, a MO message may be received and may provide information responsive to the sent (MT) message. In some embodiments, at least one of the MT messages and/or MO messages may be validated. Some embodiments provide that validation may include comparing content in a MO to a set of valid response messages. In some embodiments, validation information may be stored and may be included in an audit trail.

Some embodiments may include generating and assigning unique identifiers for campaigns, studies, clients, users, potential subjects, subjects, message recipients, and/or messages, among others. In some embodiments, unique identifiers can be used to query delivery receipts and/or MO responses to delete specific messages and/or to update specific messages. In some embodiments, unique identifiers may be used to match a MT message with a MO message that is received. In some embodiments, identifiers, input data, message schedule data, sent messages, delivery confirmations, received messages, and/or audit trail data may be stored in a data base and may be selectively encrypted therein. Some embodiments provide that messages may be transmitted and/or received in multiple languages and that services may be globally provided using telecommunications operators in a multiple different foreign countries.

Figure 4:
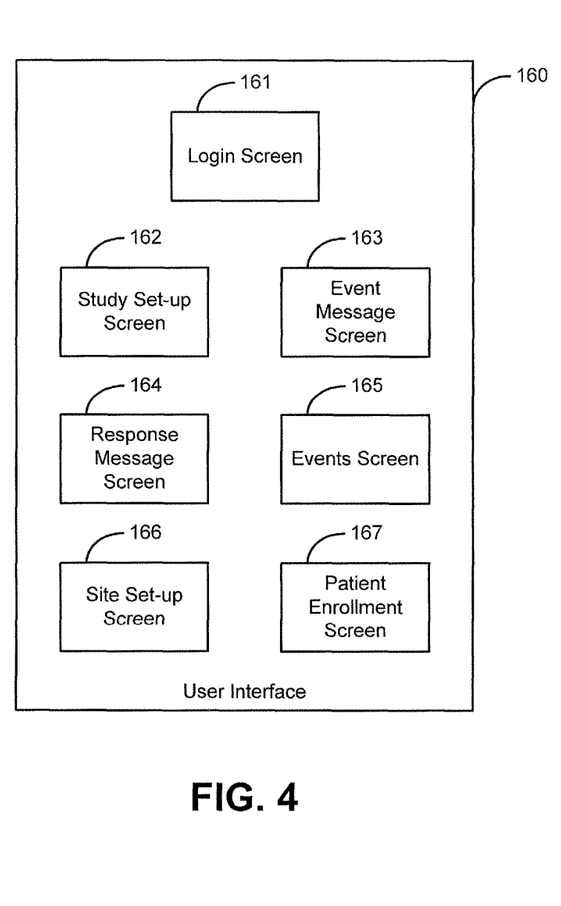
FIG. 4 is a block diagram illustrating a user interface according to some embodiments of the present invention.

Reference is now made to FIG. 4, which is a block diagram illustrating a user interface 160 according to some embodiments of the present invention. In some embodiments, the user interface 160 may include a login screen 161 that may be configured to permit selective levels of system access to authorized users. A login screen 161 may include fields to enter a site destination, a user login name and/or a password among others. In some embodiments, the login screen 161 may be configured to provide a limited number of login attempts before preventing access for a given user.

In some embodiments, a user interface 160 may include a study set-up screen 162. Some embodiments provide that a study set-up screen 162 may include entry fields for providing a study name, a program code, and/or a status that is configured to indicate whether the study is in a live or test mode. In some embodiments, the study set-up screen 162 may be configured to receive patient identifier format information, such as length and/or alpha-numeric content format, email subject data, email sender data, study graphical representations, such as, for example, a logo, and additional notes and/or help text. Although illustrated herein as a single study set-up screen 162, some embodiments provide that the study set-up screen 162, as well as other screens disclosed herein, may include multiple screens that may be used collectively to receive, display, evaluate and/or edit data.

In some embodiments, message templates may be available for a user to select. Message templates may include preconfigured messages and/or message formats that may be populated with user and/or sponsor-specific data. Some embodiments provide that the message templates and the user and/or sponsor-specific data may be provided in a message data storage device. In some embodiments, the message template may be stored in the message data storage and the user and/or sponsor-specific data may be received from a user and/or sponsor-controlled storage device such that the messages are dynamically generated before transmission. Some embodiments provide that a message template can be associated with a message template identifier that may be used to specify which of a plurality of message templates is to be used.

In some embodiments, a message template may include a multilingual function. For example, the message template may be operable to be expressed in one or more of multiple different languages. Some embodiments provide that a message template may include multiple customizable placeholders. In some embodiments, the multiple customizable placeholders may include a subject identifier, a nurse's name, and/or a doctor's name, among others.

In some embodiments, a user interface 160 may include an event message screen 163 that may include entry fields for entering, editing and/or deleting messages. Some embodiments provide that the event message screen 163 may display, for at least a portion of the messages, relevant data such as, for example, message name, message type, message content, message template and/or template identifier, and/or text, message timing relative to events, a transmission time, and/or recipient data and/or class, among others. In some embodiments, the message content may include text and/or graphical data, including, for example, barcodes, uniform resource locators (URL's), multimedia messaging service (MMS) messages, and/or other media capable of being delivered via mobile communications devices. Some embodiments provide that the message content may be provided in MO and/or MT messages.

In some embodiments, a user interface 160 may include a response message screen 164 that includes entry fields for entering, editing and/or deleting MT messages that are responsive to MO messages. Some embodiments provide that the response message screen 164 may display, for at least a portion of the messages, relevant data including the name of the MT message that the MO message was responsive to, when the responsive MO message is received, the content of the responsive MT message, the recipient data and/or class, the name of the responsive MT message, and/or the type of responsive MT message, among others.

In some embodiments, the user interface 160 may include an events screen 165 that may include entry fields corresponding to an event schedule based on client and/or sponsor requirements. In this regard, an event schedule may be generated that relates the messages to specific events. Some embodiments provide that the first event may be a baseline event, which may be used to automatically generate other event dates using relative temporal parameters that may be entered in the events screen 165. In some embodiments, event information including an event number, an event name, event timing, a schedule deviation tolerance value, message delivery options, and/or save and/or display options, among others, may be displayed, entered, edited and/or deleted for each event. Some embodiments provide that the events screen 165 may provide tolerance ranges corresponding to the event schedule to provide that messages may be sent in compliance with a study protocol. In some embodiments, the tolerance ranges may correspond to a preferred message schedule that may be defined by, for example, a sponsor, user and/or patient, among others.

In some embodiments, the user interface 160 may include a site set-up screen 166 that is configured to receive data and/or information regarding a hospital/clinic (in the case of a healthcare related campaign), and/or other facility and/or any other location including, for example, a specific country. The site set-up screen 166 may be used to enter information including date format, time zone, and/or message translations, among others. In some embodiments, a site may be configured to include more than one language. The site set-up screen 166 may provide for multiple selections corresponding to the site. Some embodiments provide that information corresponding to site messages may be entered, displayed and/or edited including site number, date format, time zone, language(s), campaign name, message name, message content and/or text, a time-out duration value, time-out units, invalid text, one or more valid responses, number of valid attempts, and/or response triggers, among others. In this manner, for each campaign, messages may be sent via a variety of networks that may vary by country, region, site and/or location. In some embodiments, campaigns may include multiple different communication modes including, but not limited to, one and/or two way messaging, among others that may be country, region, site and/or location specific. In some embodiments, the message translations may include placeholders and/or custom fields such as event date and/or the subject identifier, among others to provide a personalized message.

In some embodiments, the user interface 160 may include a patient enrollment screen 167. The patient enrollment screen 167 may include fields for entering, editing and/or deleting information regarding enrollment of a patient. Although not illustrated herein, some embodiments may include a patient withdrawal screen and/or a patient information editing screen. Some embodiments provide that a patient identifier and patient contact information, such as, for example, a phone number and/or email address may be entered. In some embodiments, the first event, which may be the baseline event may be displayed and/or edited. Some embodiments provide that other events that may be determined as a function of the first event may be displayed and/or edited. In this manner, the patient enrollment screen 167 may provide flexibility regarding specific patient/subject requirements, preferences and/or limitations. The patient enrollment screen 167 may provide multiple selection language selections, medication dosages, medication types, diagnosis, and/or prescription refill quantities, among others, that have been specified in the site set-up screen 166.

Figure 5:
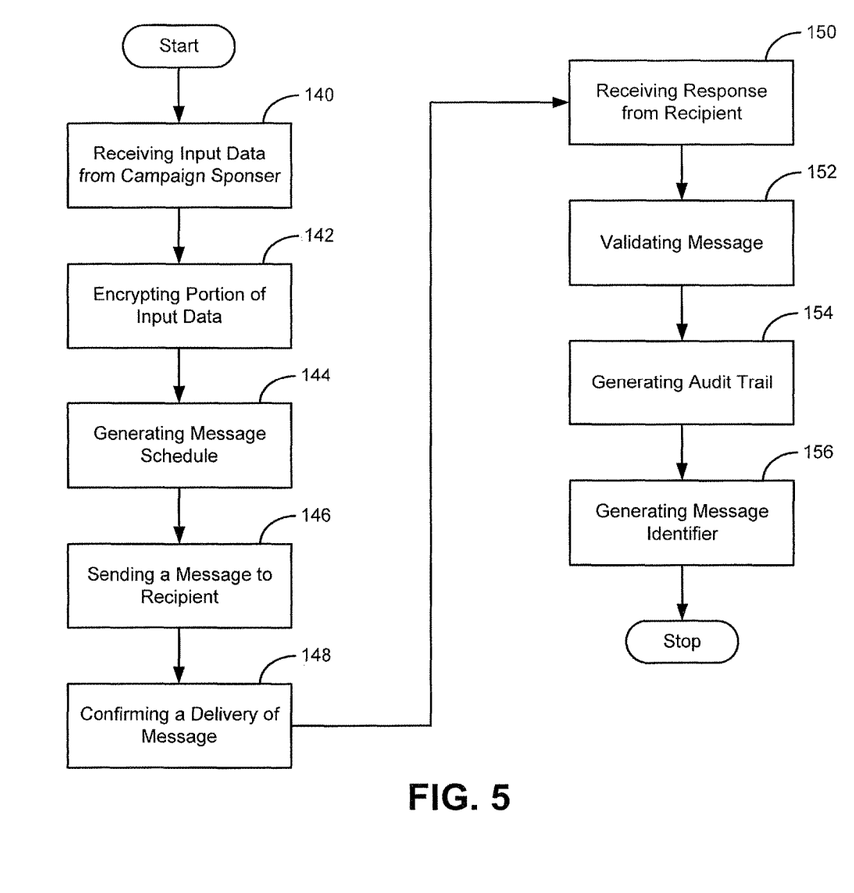
FIG. 5 is a block diagram illustrating operations for providing compliant messaging services according to some embodiments of the present invention.

Reference is now made to FIG. 5, which is a block diagram illustrating operations for providing healthcare compliant messaging services according to some embodiments of the present invention. The functions according to blocks 140-146 are discussed above regarding FIG. 3 and are not repeated herein. Methods may further include confirming a delivery of at least one of the multiple messages (block 148). In some embodiments, the delivery confirmation and/or message content may be sent to the campaign sponsor and/or maintained in a messaging service database. Some embodiments provide that delivery confirmation and/or message content may be provided and/or reported online via a network such as, for example, the Internet. In this manner, a sponsor may access delivery confirmation and/or content in a convenient and/or secure manner. In some embodiments, a logical sequence may be initiated responsive to the content of the MO message and/or delivery confirmation.

Some embodiments include receiving a response from the recipient (block 150). For example, a MO message may be sent in response to a MT message. Some embodiments may include validating at least one of the MT messages and/or MO messages (block 152). Some embodiments provide that validating may include comparing content in a MO to a set of valid response messages.

Some embodiments include generating an audit trail that is configured to provide a historical record corresponding to ones of the MT and/or MO messages (block 154). In some embodiments, validation information may be stored and may be included in an audit trail. In some embodiments, the audit trail may include a history that captures all modifications, generation and/or transmissions of each message and/or the timestamp corresponding to each of the activities, user name and/or events. In some embodiments, the audit trail may include data that is encrypted in compliance with regulatory requirements. Embodiments may include generating a message identifier corresponding to ones of the MO and/or MT messages (block 156).

Some embodiments provide that a MT message may be responsive to an unprompted MO message. For example, an unprompted MO message maybe initiated by a user responsive to, for example, an advertisement that may be received by the user via one or more advertising media such as magazines, newspaper, television, internet and/or radio, among others.

Some embodiments provide that a MT message may be resent if a responsive MO message is not received within a user-defined time period. In some embodiments, where the MT messages are sent in a broadcast set of messages, the broadcast set of messages may be adjusted to prevent resending a message to a recipient that did respond.

In some embodiments, the compliant messaging service may be configured to comply with healthcare service specific requirements. For example, healthcare services may be regulated by codes and/or statutes including the Health Insurance Portability and Accountability Act (HIPPA) and/or rules promulgated by the Department of Health and Human Services (HHS). For example, HHS rules may include a privacy rule, which may establish regulations for the use and disclosure of Protected Health Information (PHI), and a security rule, which may deal specifically with Electronic Protected Health Information (EPHI) and identify three types of security safeguards required for compliance, including, for example, administrative, physical, and/or technical safeguards. In some embodiments, healthcare services may be regulated by the Food and Drug Administration via, for example, 21 C.F.R. § 11. Although discussed in the context of healthcare specific services, however, the disclosure herein is not so limited.

Some embodiments include receiving a response from a subject via a mobile terminal. As discussed above regarding FIG. 1, a MO message may be received and may provide information responsive to the sent (MT) message. In some embodiments, at least one of the MT messages and/or MO messages may be validated. Some embodiments provide that validation may include comparing content in a MO to a set of valid response messages. In some embodiments, validation information may be stored and may be included in an audit trail.

Some embodiments may include generating and assigning unique identifiers for campaigns, studies, clients, users, potential subjects, subjects, message recipients, and/or messages, among others. In some embodiments, unique identifiers can be used to query delivery receipts and/or MO responses to delete specific messages and/or to update specific messages. In some embodiments, unique identifiers may be used to match a MT message with a MO message that is received. In some embodiments, identifiers, input data, message schedule data, sent messages, delivery confirmations, received messages, and/or audit trail data may be stored in a data base and may be selectively encrypted therein. Some embodiments provide that messages may be transmitted and/or received in multiple languages and that services may be globally provided using redundant telecommunications operators in a multiple different foreign countries.

In the drawings and specification, there have been disclosed typical embodiments of the invention and, although specific terms are employed, they are used in a generic and descriptive sense only and not for purposes of limitation, the scope of the invention being set forth in the following claims. Moreover, those skilled in the art will readily appreciate that many modifications are possible to the exemplary embodiments that are described in detail in the present specification that do not materially depart from the novel teachings and advantages of this invention. Accordingly, all such modifications are intended to be included within the scope of this invention as defined in the claims and equivalents thereof.

That which is claimed is:

1. A method of enhancing reliability of healthcare compliant messaging services, the method comprising:
   receiving input data corresponding to a study associated with a new drug and/or drug application from a pharmaceutical provider;
   encrypting at least a portion of the input data;
   generating, under control of one or more computer systems, a message schedule that is based on the input data and that includes message content, recipient identification data and temporal data corresponding to a plurality of messages;
   sending one of the plurality of messages to a corresponding recipient, using a message transmitter, wherein the message transmitter is configured to reduce risks associated with integration complexity, and provide redundant communications network paths to transmit the one of the plurality of messages;
   confirming a delivery of the one of the plurality of messages sent to the corresponding recipient;
   receiving a response from the corresponding recipient to the one of the plurality of messages, wherein the response is sent by a mobile terminal without input via a direct human communication interface;
   validating the one of the plurality of messages, wherein validating comprises comparing the one of the plurality of messages to a plurality of valid messages;
   generating an audit trail that is configured to create a historical record corresponding to each of the plurality of messages; and
   generating a unique identifier corresponding to the one of the plurality of messages.

2. A method for enhancing reliability of compliant messaging services, the method comprising:
   receiving input data corresponding to a study associated with a new drug and/or drug application from a pharmaceutical provider;
   encrypting at least a portion of the input data;
   generating, under control of one or more computer systems, a message schedule that is based on the input data and that includes message content, recipient identification data and temporal data corresponding to a plurality of messages base on the input data;

sending one of the plurality of messages to a corresponding recipient, using a message transmitter, wherein the message transmitter is configured to reduce risks associated with integration complexity, and provide redundant communications network paths to transmit the one of the plurality of messages;

receiving a response to the one of the plurality of messages, wherein the response is sent by a mobile terminal without input via a direct human communication interface; and generating an audit trail that is configured to create a historical record corresponding to each of the plurality of messages, wherein the audit trail includes message version data.

3. The method according to claim 2, further comprising confirming a delivery of the one of the plurality of messages sent to the corresponding recipient.

4. The method according to claim 2, further comprising, upon receiving indication of delivery failure of the one of the plurality of messages, sending the one of the plurality of messages via a different redundant communication network route and/or channel.

5. The method according to claim 4, wherein receiving indication of delivery failure of the one of the plurality of messages comprises failure to confirm a delivery of the one of the plurality of messages.

6. The method according to claim 4, wherein receiving indication of delivery failure of the one of the plurality of messages comprises receiving indication of delivery failure from a communications network resource.

7. The method according to claim 2, further comprising validating the one of the plurality of messages and/or a response from the corresponding recipient, wherein validating comprises comparing the one of the plurality of messages and/or the response from the corresponding recipient to a plurality of valid messages.

8. The method according to claim 2, wherein the audit trail includes message timestamp data corresponding to any changes to the one of the plurality of messages, delivery attempt data including corresponding timestamp data, response data and/or user identification data.

9. The method according to claim 2, wherein the compliant messaging services are compliant with healthcare and/or pharmaceutical service specific requirements.

10. The method according to claim 2, further comprising receiving a response from the corresponding recipient to the one of the plurality of messages.

11. The method according to claim 2, further comprising generating a unique identifier corresponding to the one of the plurality of messages.

12. The method according to claim 2, wherein the one of the plurality of messages comprise a self-executing portion therein.

13. The method according to claim 12, wherein the self-executing portion is caused to execute responsive to a temporal event, an access event and/or a transmission event.

14. The method according to claim 12, wherein the self-executing portion comprises a delete function, that when executed, causes the one of the plurality of messages to self-destruct.

15. The method according to claim 12, wherein the self-executing portion comprises a uniform resource locator (URL).

16. A computer program product for enhancing reliability of compliant messaging services, the computer program product comprising a non-transitory computer usable storage medium having computer readable program code embodied in the medium, the computer readable program code configured to:

receive input data corresponding to a study associated with a new drug and/or drug application from a pharmaceutical provider;

encrypt at least a portion of the input data;

generate, under control of one or more computer systems, a message schedule that is based on the input data and that includes message content, recipient identification data and temporal data corresponding to a plurality of messages base on the input data;

send, over a communications network one of the plurality of messages to a corresponding recipient mobile terminal, using a message transmitter, wherein the message transmitter is configured to reduce risks associated with integration complexity, and provide redundant communications network paths to transmit the one of the plurality of messages;

receiving a response to the one of the plurality of messages from the corresponding recipient mobile terminal, wherein the response is sent by the corresponding recipient mobile terminal without input via a direct human communication interface; and generate an audit trail that is configured to create a historical record corresponding to each of the plurality of messages, wherein the audit trail includes message version data.

17. A healthcare compliant message system for enhancing reliability of healthcare compliant messaging services, the system comprising:

a campaign message manager that receives healthcare related input data that corresponds to a study associated with a new drug and/or drug application from a pharmaceutical sponsor and subject data corresponding to study subjects who are participating in the study associated with a new drug and/or drug application, and generates message schedule data corresponding to the healthcare related input data and the subject data and that defines message delivery and message content information;

a first set of one or more processors configured to: receive the message schedule data, transmit a message that correspond to the message schedule data to a mobile terminal using a message transmitter, and receive a message originating from the mobile terminal responsive to a transmitted message, wherein the message originating from the mobile terminal is sent without input via a direct human communication interface, wherein the message transmitter is configured to reduce risks associated with integration complexity, and provide redundant communications network paths to transmit the one of the plurality of messages; and a second set of one or more processors configured to: generate and maintain an audit trail corresponding to messages that are transmitted to the mobile terminal.

18. The system according to claim 17, wherein the first set of one or more processors is further configured to transmit a message to the mobile terminal that is responsive to a mobile terminal originated message that is an initiating message responsive to an external information source.

19. The system according to claim 17, wherein the campaign message manager comprises:

a user interface that receives the healthcare related input data via an administrative user, wherein the user interface comprises an end user portion that receives the subject data;

a set of one or more processors configured to: use subject data that is received via the user interface to populate an enrolled study subject database corresponding to enrolled study subjects;

and a message schedule generator that uses the healthcare related input data via the user interface and the enrolled study subject database to generate the message schedule data.

20. The system according to claim 19, wherein the message schedule data includes at least one message schedule, message content, at least one reminder message, at least one message language identifier, message format and/or location-based temporal information.

21. The system according to claim 19, wherein the campaign message manager further comprises a set of one or more processors that is configured to communicate message schedule data to the first set of one or more processors.

22. The system according to claim 17, wherein the message transmitter transmits messages to at least one mobile terminal according to the message schedule; and the first set of one or more processors is further configured to receive messages originated by at least one mobile terminal.

23. The system according to claim 22, wherein the audit trail includes message version data, message timestamp data corresponding to any changes to the message, delivery attempt data including corresponding timestamp data, response data corresponding to messages received by the first set of one or more processors and/or user identification data.

24. The system according to claim 22, further comprising a set of one or more processors that is configured to: validate received messages originated by the at least one mobile terminal to determine if one of the received messages are valid responses to respective one of the transmitted messages, wherein the audit trail further includes validation data.

25. The system according to claim 17, wherein the message schedule data includes a message frequency restriction corresponding to transmitted messages.

26. The system according to claim 25, wherein the message frequency restriction restricts quantity of messages that can be transmitted within a defined temporal duration.

27. The system according to claim 17, wherein the campaign message manager generates the message schedule data via at least one message template that includes a predefined message format and wherein the healthcare related input data includes at least one message template identifier that corresponds to the at least one message template.

28. The system according to claim 27, wherein the at least one message template comprises a multilingual function, wherein the at least one message template is operable to be expressed in a plurality of languages.

29. The system according to claim 27, wherein the at least one message template comprises a plurality of customizable placeholders.

* * * * *